US00PP35126P2

(12) United States Plant Patent
Camus

(10) Patent No.: US PP35,126 P2
(45) Date of Patent: Apr. 25, 2023

(54) ***HYDRANGEA* 'CAMCHO45'**

(50) Latin Name: ***Hydrangea* x *macrophylla***
Varietal Denomination: CAMCHO45

(71) Applicant: Sicamus, Angers (FR)

(72) Inventor: Christophe Camus, Angers (FR)

(73) Assignee: SICAMUS

( * ) Notice: Subject to any disclaimer, the term of this patent is extended or adjusted under 35 U.S.C. 154(b) by 0 days.

(21) Appl. No.: 17/958,072

(22) Filed: Sep. 30, 2022

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Cassandra Bright

(57) ABSTRACT

A new and distinct cultivar of *Hydrangea* plant named 'CAMCHO45' is disclosed, characterized by lace-cap inflorescences with large, distinctly concave pure white sepals. Plants have rounded habits, dark green foliage, and very dark purple stems. The new variety is a *Hydrangea*, typically produced as an outdoor ornamental plant.

2 Drawing Sheets

Figure 1:
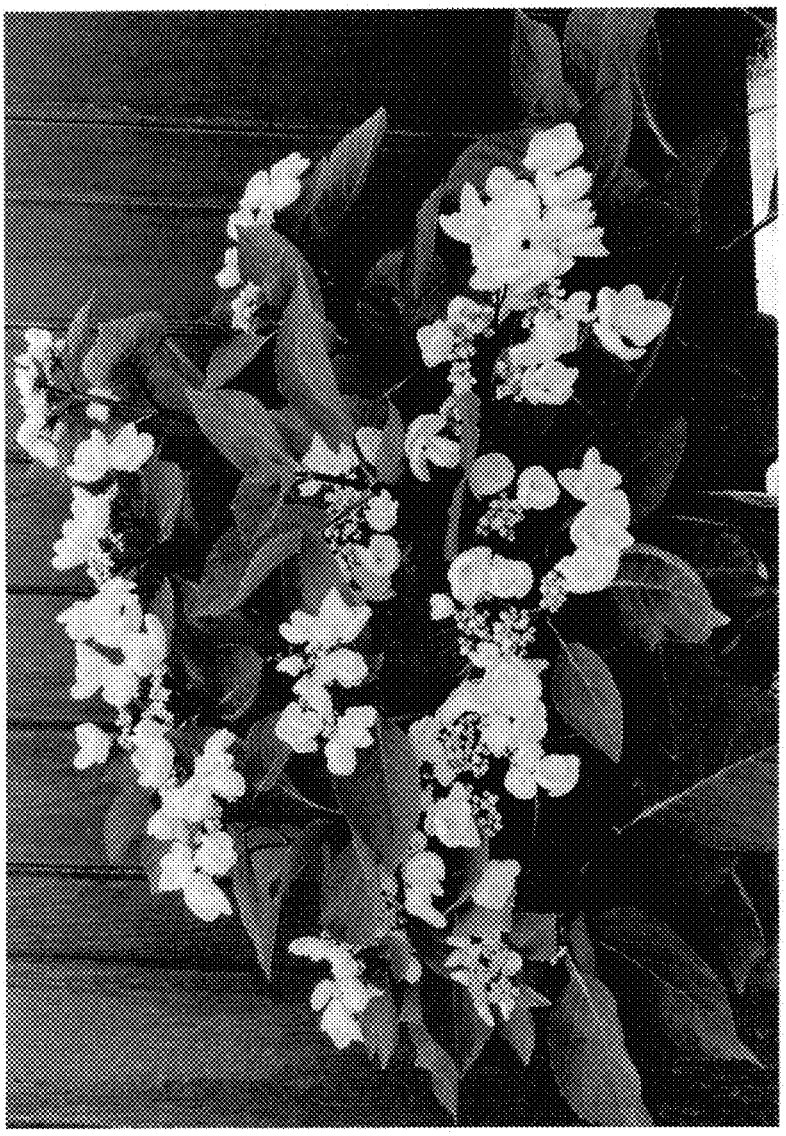

Latin name of the genus and species: *Hydrangea* x *macrophylla.*
Variety denomination: 'CAMCHO45'.

BACKGROUND OF THE INVENTION

The new cultivar is a product of a planned breeding program conducted by the inventor, at a commercial nursery in Angers, France. The crossing resulting in the new variety was made during 2008.

The seed parent is an unpatented proprietary variety of *Hydrangea macrophylla*. The pollen parent is a different unpatented proprietary variety of *Hydrangea macrophylla.*

The new variety was found and selected by the inventor in 2009 at the same nursery in Angers, France.

Asexual reproduction of the new cultivar 'CAMCHO45' was first performed during July of 2010 in Angers, France, by vegetative cuttings. Through subsequent propagation, multiple additional generations have been reproduced, having shown that the unique features of this cultivar are stable and reproduced true to type.

SUMMARY OF THE INVENTION

The cultivar 'CAMCHO45' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAMCHO45.' These characteristics in combination distinguish 'CAMCHO45' as a new and distinct *Hydrangea* cultivar:

1. Very dark purple stems.
2. Pure white sepals.
3. Sepals are very large and strongly concave.
4. Very floriferous.

PARENT COMPARISON

Plants of 'CAMCHO45' are similar to plants of the seed parent in most horticultural characteristics, however, plants of 'CAMCHO45' differ in the following:

1. The new variety has very dark purple stems; the seed parent has green stems.
2. Sepals are very large and strongly concave; a characteristic not found in the seed parent.
3. Plants of the new variety are more floriferous than plants of the seed parent.

Plants of 'CAMCHO45' are similar to plants of the pollen parent in most horticultural characteristics, however, plants of 'CAMCHO45' differ in the following:

1. Stems of the pollen parent are not as dark purple as those of 'CAMCHO45'.
2. Sepals are very large and strongly concave; a characteristic not found in the pollen parent.

COMMERCIAL COMPARISON

Plants of the new cultivar *Hydrangea* 'CAMCHO45' can be compared to the commercial variety *Hydrangea macrophylla* 'Nigra', unpatented. Plants of 'CAMCHO45' are similar to plants of 'Nigra' in most horticultural characteristics, however, plants of 'CAMCHO45' differ in the following:

1. The new variety has lace-cap inflorescences; this comparator is a mophead.
2. The new variety has darker green foliage than this comparator.
3. The new variety is more compact than this comparator.
4. The new variety has sturdier stems than this comparator.
5. The new variety has white flowers; 'Nigra' has either pink or blue flowers, depending upon soil conditions.

Plants of the new cultivar *Hydrangea* 'CAMCHO45' can be compared to the commercial variety *Hydrangea macrophylla* 'White', unpatented. Plants of 'CAMCHO45' are similar to plants of 'White' in most horticultural characteristics, however, plants of 'CAMCHO45' differ in the following:

1. Stems on new variety are very dark purple; stems of this comparator are green.

2. The new variety has lace-cap inflorescences; this comparator is a mophead.
3. Sepals on new variety are very large and strongly concave; sepals of this comparator are smaller and not concave.
4. The new variety is more compact than this comparator.
5. The new variety has sturdier stems than this comparator.

BRIEF DESCRIPTION OF THE PHOTOGRAPHS

The accompanying photograph in FIG. 1 illustrates in full color a typical plant of 'CAMCHO45' grown outdoors Camarillo, Calif. This plant is approximately 2-3 years old, grown in a #5 container.

Figure 2:
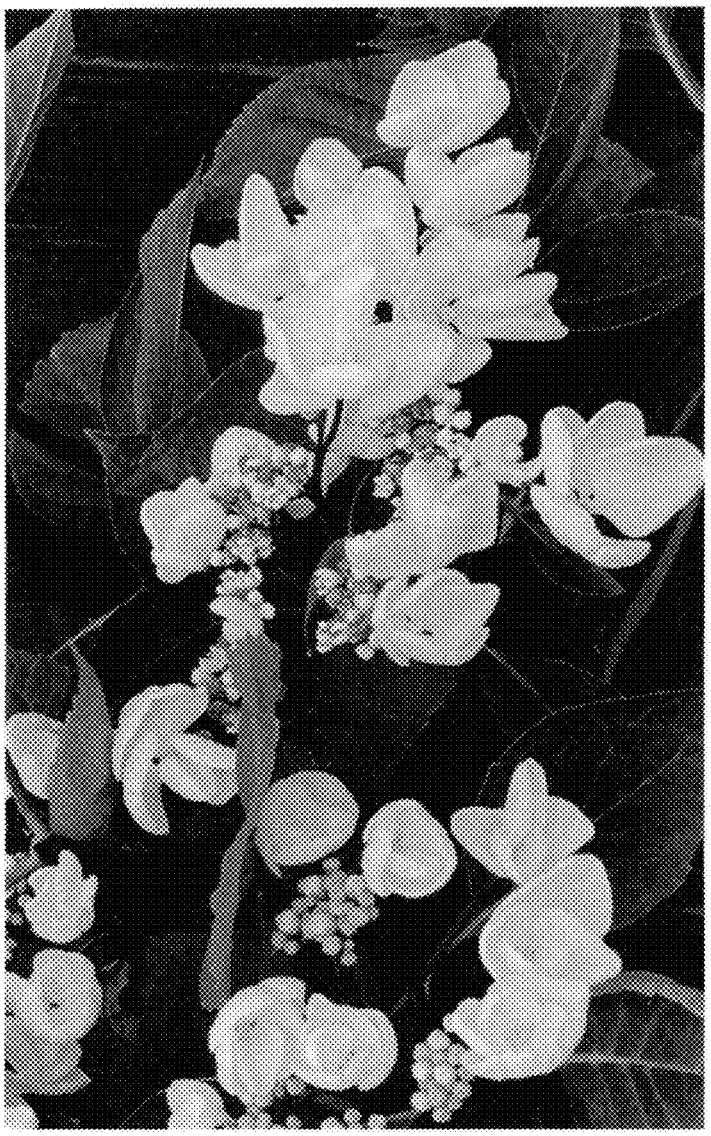

FIG. 2 illustrates in full color a close up of the flowers of 'CAMCHO45'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'CAMCHO45' plants grown outdoors in Camarillo, Calif. The plants were about 2 years old. Temperatures ranged from 12° C. to 15° C. at night to 18° C. to 27° C. during the day. No artificial light, photoperiodic treatments were given to the plants. Measurements and numerical values represent averages of typical plant types.

Botanical classification: *Hydrangea macrophylla* 'CAMCHO45'.

PROPAGATION

Typical method: Softwood cuttings.
Root initiation: Approximately 20 days.
Time to produce rooted cutting: 60 days during summer.
Roots: Thick to thin, freely branching, fibrous, dense. White to brown in color, not accurately measured with RHS chart.

PLANT

Plant shape: Round.
Growth habit: Outward and upward.
Height: 55 cm.
Plant spread: 60 cm.
Pot size of plant described: 3-gallon container.
Age of plant described: Approximately 2 years.
Growth rate: Moderate.
Plant vigor: Good.
Stems/branches:
- *Branching.*—Basal.
- *Number of main stems/branches.*—12 to 15.
- *Shape.*—Rounded.
- *Color.*—Immature: RHS Greyed-Purple N186B. Mature: RHS Greyed-Purple N186A. Old growth: RHS Greyed-Purple N186B striated Greyed-Brown N199B.
- *Length.*—35 to 42 cm.
- *Width.*—7 to 11 mm.
- *Aspect.*—Mainly straight, outermost branch slightly concave. Angle about 15° to 45°.
- *Strength.*—Moderately strong.
- *Texture.*—Glabrous, no lenticels. Small ridges detectable.
- *Internode length.*—4.5 to 7 cm.

FOLIAGE

Leaf:
- *Arrangement.*—Opposite.
- *Shape.*—Ovate.
- *Length.*—11 cm.
- *Width.*—7 to 9 cm.
- *Apex.*—Acuminate.
- *Base.*—Obtuse to broad tapered.
- *Margin.*—Dentate.
- *Texture of top surface.*—Glabrous.
- *Texture of bottom surface.*—Glabrous.
- *Color.*—Young foliage upper side: Near RHS Green 137A. Young foliage under side: Near RHS Green 138A. Mature foliage upper side: Near RHS Green 139A. Mature foliage, under side: Near RHS Green 137D.

Venation:
- *Type.*—Pinnate.
- *Color.*—Upper side: Near RHS Yellow-Green 144B. Under side: Near RHS Yellow-Green 145A, near petiole attachment strongly flushed Greyed-Purple 187A.

Petiole:
- *Length.*—2 cm to 3 cm.
- *Width.*—4 mm.
- *Color.*—Upper side: RHS Yellow-Green 145A, flushed Greyed-Purple 187A. Under side: RHS Yellow-Green 145A, nearly completely covered in Greyed-Purple 187A flush. Upper side: Glabrous. Under side: Glabrous.

INFLORESCENCE

Natural flowering season: Summer.
Inflorescence type: Lace-cap.
Corymb:
- *Shape.*—Flat, disc shaped.
- *Height.*—5 cm.
- *Diameter.*—Average range 12 to 18 cm.

Fragrance: None.
Sterile flowers:
- *Flowers per inflorescence.*—10 to 15.
- *Aspect.*—Upright facing flower composed of strongly concave sepals.
- *Shape.*—Round.
- *Arrangement.*—Overlapping whorl.
- *Diameter.*—4.0 cm. Petals remain concave, not flattening out.
- *Depth.*—3.0 cm(excluding pedicel).
- *Persistent or self-cleaning.*—Persistent.

Bud:
- *Bud length.*—5 mm.
- *Bud diameter.*—5 mm.
- *Bud shape.*—Sphere.
- *Bud color.*—RHS Green-White 157A.

Pedicel:
- *Length.*—3 cm.
- *Diameter.*—2 mm.

*Angle.*—About 135° from center.
*Strength.*—Good, flexible.
*Texture.*—Glabrous.
*Color.*—RHS Red-Purple 59A. Base Greyed-Purple 187A.

Fertile flowers:
*Flowers per inflorescence.*—About 120 to 150.
*Shape.*—Stellate.
*Diameter.*—5 mm.
*Depth.*—3 mm.
*Persistent or self-cleaning.*—Self-cleaning.

Bud:
*Bud length.*—3 mm.
*Bud diameter.*—3 mm.
*Bud shape.*—Sphere.
*Bud color.*—RHS Green-White 157A.

Sepal:
*Number per flower.*—5.
*Arrangement.*—Stellate.
*Shape.*—Obovate.
*Tip.*—Acute.
*Base.*—Truncate.
*Margin.*—Entire.
*Length.*—3 mm.
*Width.*—2 mm.
*Texture.*—Upper side: Glabrous. Under side: Glabrous.
*Color.*—When Opening, Upper side: RHS Green-White 157C. When Opening, Under side: RHS Green-White 157C. Fully Opened, Upper side: RHS White 155C. Fully Opened, Under side: RHS White 155C.

Pedicel:
*Length.*—3 to 7 mm.
*Diameter.*—2 mm.
*Angle.*—15° to 135°.
*Strength.*—Good.
*Texture.*—Glabrous.
*Color.*—RHS Red-Purple 59A. Base Greyed-Purple 187A.

REPRODUCTIVE ORGANS

Sterile flower: Central, globular structure with no definable parts.

Fertile flower:

Stamen:
*Number.*—10 to 12.
*Filament length.*—3 to 4 mm.
*Filament color.*—RHS White 155D.

Anther:
*Shape.*—Rounded, basifixed.
*Length.*—About 1 mm.
*Color.*—RHS White 155A.
*Pollen amount.*—None observed.

Pistil:
*Number.*—1.
*Length.*—3 mm.

Stigma:
*Shape.*—3-parted.
*Color.*—RHS White 155A.
*Style length.*—2 mm.
*Style color.*—RHS White 155D.
*Ovary color.*—RHS White 155D.

OTHER CHARACTERISTICS

Disease resistance: Neither resistance nor susceptibility to the normal diseases and pests of *Hydrangea* has been observed.

Drought tolerance: None.

Temperature tolerance: USDA Zones 6 to 9 reliably, Zone 5 with protection from the cold.

Fruit/seed production: Not observed to date.

What is claimed is:

1. A new and distinct cultivar of *Hydrangea* plant named 'CAMCHO45' as herein illustrated and described.

* * * * *